United States Patent [19]

Hall et al.

[11] Patent Number: 4,863,967
[45] Date of Patent: Sep. 5, 1989

[54] N,N-DIAMINOPHTHALAMIDES

[75] Inventors: Iris H. Hall, Chapel Hill; Steven D. Wyrick, Durham, both of N.C.

[73] Assignee: Research Corporation, New York, N.Y.

[21] Appl. No.: 874,938

[22] Filed: Jun. 16, 1986

[51] Int. Cl.$^4$ ............... A61K 31/615; A61K 31/165; C07C 109/10
[52] U.S. Cl. ................... 514/615; 564/149; 564/150; 514/166
[58] Field of Search ............... 564/149, 150; 514/615, 514/166

[56] References Cited

U.S. PATENT DOCUMENTS

| | | | |
|---|---|---|---|
| 2,615,862 | 10/1952 | McFarlane et al. | 564/149 X |
| 3,222,372 | 12/1965 | Weidinger et al. | 564/149 X |
| 3,502,685 | 3/1970 | Gevirtz et al. | 260/294 |
| 3,631,005 | 12/1971 | Fan | 564/149 X |
| 4,158,014 | 6/1979 | Musser | 260/558 |
| 4,310,545 | 1/1982 | Shepherd | 424/310 |
| 4,311,846 | 1/1982 | Shepherd | 546/226 |

FOREIGN PATENT DOCUMENTS 55-157550  8/1980  Japan .

OTHER PUBLICATIONS

Chemical Abstracts 105:9100(h) Dec. 1986.
Chemical Abstracts 65.7865b (1966).
Chemical Abstracts 54:759g (1960).
Murphy et al. *Pharmaceutical Research*, vol. 3, No. 2, pp. 93–101 (1986).
Bee et al. *Yao Hsiiek Hsueh Pao*, 7, 109–118 (1959).
Fournier et al. *Therapie*, 21 (3), 787–796 (1966).
Offe et al., Z. Naturforsch, vol. 7B, 449–455, 1952.

*Primary Examiner*—Charles F. Warren
*Assistant Examiner*—Carolyn S. Greason
*Attorney, Agent, or Firm*—Scully, Scott, Murphy & Presser

[57] ABSTRACT

A compound having the structural formula

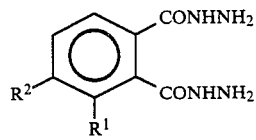

wherein $R^1$ and $R^2$ are the same or different and are hydrogen, $C_1$–$C_6$ alkyl, halogen or $C_1$–$C_4$ alkoxy is disclosed. These compounds demonstrate utility as hypolipidemic agents.

The present invention is also directed to a process for controlling lipidemia in mammals comprising treating mammals with a lipidemia controlling effective amount of the above-defined compound.

Yet another aspect of the present invention is embodied in a pharmaceutical composition comprising the above compound and a pharmaceutically acceptable carrier therefor.

13 Claims, No Drawings

N,N-DIAMINOPHTHALAMIDES

BACKGROUND OF THE DISCLOSURE

1. Field of the Invention

The present invention is directed to a process for controlling lipidemia. More specifically, the present invention is directed to a process for controlling lipidemia in mammals by treating that condition with a generic class of N,N-diaminophthalamides.

2. Background of the Prior Art

Hyperlipidemia, a condition associated with elevated serum cholesterol, phospholipid and/or triglyceride blood levels, is the base cause of a whole class of illnesses which exact a terrible toll in death and infirmity as well economic loss associated with lost productive activity and expensive medical treatment. It is only necessary to mention one of the most serious conditions known in man, atherosclerosis, a hyperlipidemic induced illness, to appreciate the importance of developing treatment regimes effective in controlling this condition. Recent scientific studies indeed establish that coronary heart disease is related to blood lipid concentration. *J, Am. Med. Assn.,* Vol. 251, 351-373, Jan. 20, 1984; *N. Engl. J. Med.,* Vol. 314, 138-144, Jan. 16, 1986.

Because of the importance of hyperlipidemia, many compounds have been proposed to lower serum cholesterol, phospholipid and triglyceride blood levels in mammals. For example, U.S. Pat. No. 4,499,303 discloses a novel class of N-benzoyl, N-benzoylsulfamates and benzoylsulfonamides useful in this application.

Another class of compounds disclosed as useful in reducing serum cholesterol and triglyceride blood levels in mammals is set forth in U.S. Pat. No. 4,395,417. This patent describes the use of cyclic imides, diones, reduced diones and analogs thereof useful in this application.

Certain compounds within the generic class conveniently referred to as N,N-diaminophthalamides, are known in the art. However, a subgeneric class of ortho-hydrazinocarbonyl benzoic acid hydrazides is new and not known in the prior art. However, there are references in the prior art to classes of structurally somewhat similar to these new ortho-hydrazinocarbonyl benzoic acid hydrazides.

H. A. Offe et al., *Z. Naturforsch,* Vol. 7B, 446-462 (1952) sets forth a table of benzoic acid hydrazides without any recitation of utility. None of those compounds are hydrazinocarbonyl benzoic acid hydrazides.

Japanese Patent Publication 55-157,550 discloses a class of compounds the most relevant of which is

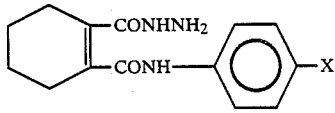

where X is halogen, preferably chlorine.

U.S. Pat. No. 3,502,685 describes an ortho substituted hydrazinocarbonyl substituted benzoic acid hydrazide having the formula

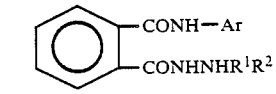

where Ar is naphthyl, dichlorophenyl or trichlorophenyl; $R^1$ and $R^2$ are hydrogen, lower alkyl or compositely forms a non-aromatic heterocycle; also if $R^1$ is hydrogen $R^2$ may be phenyl, naphthyl or a chloro-substituted derivative thereof. The compounds of this patent serve as herbicides.

The compound, 4-(hydrazinomethyl)benzoic acid hydrazide is the subject of U.S. Pat. No. 4,158,014. This compound can be polymerized by condensation with difunctional acid chloride to form high tensile strength films.

Novel 4-(polyfluoroalkylamino)substituted phenyl compounds are described in U.S. Pat. No. 4,310,545 as being useful in the treatment of hyperlipidemia. Similarly, the same patentee, in U.S. Pat. No. 4,311,846, teaches a similar class of compounds, also recited to possess hypolipidemic and antiatherosclerotic antivity, the 4-[(monosubstituted alkyl)amino]benzoic acid and analogs thereof.

The above analysis of the prior art is provided in order to establish that there is no disclosures of hypolipidemic agents whose structures are closely related to those of the present invention. Thus, there is no suggestion in the art for providing a new class of ortho-hydrazinocarbonyl benzoic acid hydrazides useful in the treatment of hyperlipidemia.

SUMMARY OF THE INVENTION

It has now been discovered that a new class of compounds exhibits significant hypolipidemic activity in mammals at lower concentration than any of the compounds remotely similar thereto. These compounds are characterized by the ability to control lipidemia at low concentration thus eliminating many of the undesirable side effects found in the hypolipidemic agents of the prior art.

In accordance with the present invention a process is provided for controlling lipidemia comprising treating a mammal with a lipidemia controlling effective amount of a compound having the structural formula

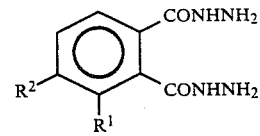

where $R^1$ and $R^2$ are the same or different and are hydrogen, halogen, $C_1$-$C_6$ alkyl or $C_1$-$C_6$ alkoxy.

In further accordance with the present invention a therapeutic composition is disclosed. This therapeutic composition comprises a lipidemia controlling effective amount of a compound having the structural formula

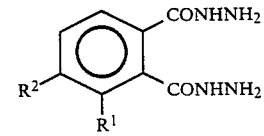

where $R^1$ and $R^2$ are the same or different and are hydrogen, halogen, $C_1$–$C_6$ alkyl or $C_1$–$C_6$ alkoxy and a pharmaceutically acceptable carrier therefore.

In still further accordance with the instant invention a compound having the structural formula

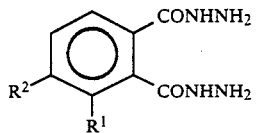

is set forth wherein $R^1$ and $R^2$ are the same or different and are hydrogen, halogen, $C_1$–$C_6$ alkyl or $C_1$–$C_6$ alkoxy.

DETAILED DESCRIPTION

The compounds of the present invention have the structural formula

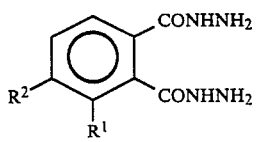

(I)

where $R^1$ and $R^2$ are the same or different and are hydrogen, $C_1$–$C_6$ alkyl, halogen or $C_1$–$C_6$ alkoxy.

More preferably, the compound of the present invention has the structural formula I where $R^1$ and $R^2$ are the same or different and are hydrogen, $C_1$–$C_4$ alkyl, chlorine, bromine or $C_1$–$C_4$ alkoxy.

Still more preferably, the compound of the present invention has the structural formula I wherein $R^1$ and $R^2$ are the same or different and are hydrogen, $C_1$–$C_2$ alkyl, chlorine or $C_1$–$C_2$ alkoxy.

Yet still more preferably, the compound of the present invention is 1,2-dihydrazinocarbonyl-3-chlorobenzene, 1,2-dihydrazinocarbonyl-4-chlorobenzene, 2,3-dihyrazinocarbonyltoluene, 3,4-dihyrazinocarbonyltoluene, 1,2-dihydrazinocarbonyl-3-methoxylbenzene or 1,2-dihydrazinocarbonyl-4-methoxybenzene.

Most preferably, the compound of the present invention is 3,4-dihydrazinocarbonyltoluene.

The instant invention also encompasses a process for controlling lipidemia in mammals. In this process a mammal whose lipid blood level is to be controlled is treated with a lipidemia controlling effective amount of a compound having the structural formula I wherein $R^1$ and $R^2$ are the same or different and are hydrogen, $C_1$–$C_6$ alkyl, halogen or $C_1$–$C_6$ alkoxy.

More preferably, a process for controlling lipidemia is provided wherein the lipid blood level of a mammal is controlled by treating the mammal with a lipidemia controlling effective amount of a compound having the structural formula I wherein $R^1$ and $R^2$ are the same or different and are hydrogen, $C_1$–$C_4$ alkyl, chlorine, bromine or $C_1$–$C_4$ alkoxy.

Still more preferably, a process for controlling lipidemia in mammals is provided wherein mammals whose lipid levels are to be controlled are provided with a lipidemia controlling effective amount of a compound having the structural formula I wherein $R^1$ and $R^2$ are the same or different and are hydrogen, $C_1$–$C_2$ alkyl, chlorine or $C_1$–$C_2$ alkoxy.

Yet still more preferably, a process for controlling lipidemia is contemplated wherein a mammal whose lipid level is to be controlled is treated with a lipidemia controlling effective amount of a compound selected from the group consisting of 1,2-dihydrazinocarbonyl-3-chlorobenzene, 1,2-dihydrazinocarbonyl-4-chlorobenzene, 2,3-dihydrazino-carbonyltoluene, 3,4-dihydrazinocarbonyltoluene, 1,2-dihydrazinocarbonyl-3-methoxybenzene and 1,2-dihydrazinocarbonyl-4-methoxybenzene.

Most preferably, a process for controlling lipidemia is described which comprises treating a mammal whose lipid level is to be controlled with a lipidemia controlling effective amount of 3,4-dihydrazinocarbonyltoluene.

It is emphasized that the term "lipidemia" refers to the lipid concentration in the blood of mammals. A whole host of mammalian diseases are associated with elevated lipid levels including elevated serum cholesterol, serum triglyceride and/or serum phospholipid blood levels. These conditions are oftentimes associated with a number of blood circulatory related diseases among which the most serious is atherosclerosis.

In a preferred embodiment of the process of the present invention a lipidemia controlling effective amount of a compound, within the contemplation of the present invention, is provided by treating a mammal with a compound as defined above in a concentration of between about 5 and 60 milligrams per kilogram of mammalian body weight per day.

More preferably, a compound within the contemplation of the present invention is utilized in the process of the instant invention provided at a rate in the range of between about 10 and 40 milligrams per kilogram of mammalian body weight per day.

Most preferably, the lipidemia controlling effective amount of a compound within the contemplation of the present invention is in the range of between about 15 and 30 milligrams per kilogram of mammalian body weight per day.

Another aspect of the present invention is directed to a pharmaceutical composition. The pharmaceutical composition of the present invention, useful in the control of lipidemia, comprises a compound having the structural formula I where $R^1$ and $R^2$ are the same or different and are hydrogen, $C_1$–$C_6$ alkyl, halogen or $C_1$–$C_6$ alkoxy and a pharmaceutically acceptable carrier therefor.

More preferably, the composition of the present invention comprises a compound within the meaning of structural formula I where $R^1$ and $R^2$ are the same or different and are hydrogen, $C_1$–$C_4$ alkyl, chlorine, bromine or $C_1$–$C_4$ alkoxy and a pharmaceutically acceptable carrier therefor.

Still more preferably, the pharmaceutical composition of the present invention comprises a compound having the structural formula defined by Compound I where $R^1$ and $R^2$ are the same or different and are hydrogen, $C_1$–$C_2$ alkyl, chlorine or $C_1$–$C_2$ alkoxy and a pharmaceutically acceptable carrier therefor.

Yet still more preferably, the pharmaceutical composition of the instant invention is a compound selected from the group consisting of 1,2-dihydrazinocarbonyl-3-chlorobenzene, 1,2-dihydrazineocarbonyl-4-chlorobenzene, 2,3-dihydrazinocarbonyltoluene, 3,4-dihydrazinocarbonyltoluene, 1,2-dihydrazinocarbonyl-3-methoxybenzene and 1,2-dihydrazinocarbonyl-4-methoxybenzene and a pharmaceutically acceptable carrier therefor.

Most preferably, the pharmaceutical composition of this invention is 3,4-dihydrazinocarbonyltoluene and a pharmaceutically acceptable carrier therefor.

Pharmaceutically acceptable carriers within the contemplation of the present invention includes solvents, dispersion media, coatings, antibacterial and antifungal agents, isotonic and absorption delaying agents and the like. The use of such media and agents for pharmaceutically active substances is known in the art. Except in so far as any conventional medium or agent is incompatible with the active ingredient of the present invention its use in the hypolipidemic pharmaceutical compositions of this invention is contemplated. Supplementary active ingredients can also be incorporated into the composition of the instant invention.

The composition of the present invention may be prepared for parenteral administration. When administered parenterally, that is, subcutaneously, intraperitoneally, intramuscularly or intravenously, the carrier may be water, buffered saline, ethanol, polyols, such as glycerol, propylene glycol or liquid polyethylene glycol, vegetable oils or the like.

To prevent microorganism contamination the carrier of the composition of the present invention may include antibacterial and/or antifungal agents such as parabens, chlorobutanol, phenol, sorbic acid, thimersal or the like. In addition, isotonic agents, for example, glucose or sodium chloride, may also be included in the pharmaceutical carrier of the composition of the present invention.

In the case of parenterally administered hypolipidemic compositions it is especially advantageous to formulate the composition in dosage units. Such formulation provides a uniform dosage thus improving active agent administration. A dosage unit means the physically discrete unit suited for unitary administration. That is, each unit contains a predetermined amount of active material calculated to produce the desired hypolipidemic effect in association with the required pharmaceutical carrier. The actual dosage unit of the composition of this invention is dictated by and directly dependent upon the unique characteristics of the active material of the instant invention and the particular hypolipidemic effect to be achieved. It is within the skill of the qualified administrator to determine the exact dosage for the subject involved.

In addition to the carriers discussed above for use in parenteral administration, additional carriers may be utilized in orally administered compositions. Carriers for orally administered pharmaceutically acceptable compositions include ingredients useful in the formation of tablets or capsules. Among the pharmaceutically acceptable carriers suitable for orally administered compositions are such excipients as starch, milk, sugar, clays and the like. The tablet or capsule carrier may include an enteric coating to make such tablet or capsule resistant to the acid and digestive enzymes of the stomach.

Although any of the pharmaceutically acceptable carriers discussed above may be combined with the active compound of the present invention, a particularly preferred carrier is carboxymethylcellulose (CMC). Specifically, a 1 percent aqueous solution of CMC is preferred for use as the carrier of the composition of the present invention.

Still another aspect of the present invention is the process for forming the compounds of the present invention. The compounds of the present invention, having the structural formula I, are prepared by reacting a 3- or 4-substituted or unsubstituted phthalic anhydride with a stoichiometric excess of hydrazine hydrate to produce the desired N,N-diaminophthalamide.

The following examples are given to illustrate the scope of the present invention. Because these examples are given for illustrative purposes only, the invention embodied herein should not be limited thereto.

EXAMPLE 1

Preparation of 1,2-Dihydrazinocarbonyl-3-Chlorobenzene (Compound No. 1)

A mixture of 3-chlorphthalic anhydride (0.01 mol) and a stoichrometric excess of hydrazine hydrate was dissolved in 25 ml of absolute ethanol. The solution was refluxed for 24 hours. The solvent was then evaporated and the product was recrystallized from ethanol.

The product, 1,2-dihydrozinocarbonyl-3-chlorobenzene, was obtained in a yield of 52 percent. The pure compound was tested, using a Thomas-Hoover melting point apparatus, to determine its melting temperture at atmospheric pressure. It was found that the melting point of this compound was in excess of 300° C.

A summary of this example is included in Table I.

EXAMPLE 2

Preparation of Compounds 2-6

Example 1 was repeated with the exception that the identity and position of the substituent on the phthalic anhydride was replaced in accordance with the desired synthesis product.

A tabulated summary of the synthesis of Compounds 2-6, which includes the identity of the substituted phthalic anhydride, and the melting point of the synthesized product is included in Table I.

TABLE I

| Compound No. | R¹ | R² | Substituted Phthalic Anhydride | Yield of Product, % | Melting Pt., °C. |
|---|---|---|---|---|---|
| 1 | Cl | H | 3-chloro | 52 | 300 |
| 2 | H | Cl | 4-chloro | 60 | 300 |
| 3 | CH₃ | H | 3-methyl | 62 | 300 |
| 4 | H | CH₃ | 4-methyl | 78 | 300 |
| 5 | OCH₃ | H | 3-methoxy | 60 | 296–298 |
| 6 | H | OCH₃ | 4-methoxy | 75 | 244–247 |

EXAMPLE 3

Hypolipidemic Activity of Compound Nos. 1-2 in Male Mice

The compounds of Table I, Compounds 1–6, were suspended in an aqueous 1 percent CMC solution and homogenized. Each of the so prepared compounds was administered intraperitoneally, in a dosage of 20 milligrams per kilogram of body weight per day, to a group of six CF₁ male mice, each weighing approximately 25 grams, for 16 days. On Days 9 and 16 blood was obtained from each of the tested mice by tail vein bleeding. The blood serum so obtained was separated by centrifugation for three minutes. Serum cholesterol levels were determined by a modification of the Leibermann-Burchard reaction, (Ness et al., *Clin. Chem. Acta.*, Vol. 10, 229 [1964]). Serum triglyceride levels were obtained on Day 16 by use of the Bio-Dynamics/bm Triglyceride Kit.

In addition to the above-described treated mice, an untreated control group of six mice were similarly tested on Days 9 and 16 to determine their serum cholesterol and serum triglyceride blood levels. Based on the results obtained for the untreated control group, the percent control, based on serum cholesterol and serum triglyceride levels of the treated mice compared to the untreated mice, was obtained.

Finally, to insure that the carrier, 1% CMC, is not the active agent a group of six CF$_1$ male mice were treated in accordance with the procedure utilized to test the compounds of the present invention with a 1% aqueous solution of CMC.

Table II reports percent control, including standard deviation, indicative of the level of confidence in these percentages, for each active compound and the CMC control.

TABLE II

| Compound No. | PERCENT CONTROL, ± STANDARD DEVIATION | | |
|---|---|---|---|
| | Serum Cholesterol | | Serum Triglycerides |
| | Day 9 | Day 16 | Day 16 |
| Control (1% CMC) | 100 ± 5 | 100 ± 6 | 100 ± 5 |
| 1 | 85 ± 6 | 73 ± 5 | 62 ± 2 |
| 2 | 68 ± 4 | 64 ± 5 | 62 ± 3 |
| 3 | 75 ± 6 | 75 ± 5 | 78 ± 3 |
| 4 | 63 ± 5 | 58 ± 3 | 52 ± 4 |
| 5 | 70 ± 4 | 55 ± 2 | 70 ± 7 |
| 6 | 54 ± 3 | 71 ± 4 | 65 ± 3 |

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the scope of the present invention should be limited only by the appended claims.

What is claimed is:

1. A composition comprising a hyperlipidemia controlling effective amount of a compound having the structural formula

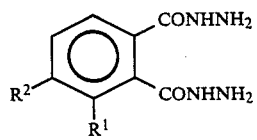

where $R^1$ and $R^2$ are the same or different and are hydrogen, $C_1-C_6$ alkyl, halogen or $C_1-C_6$ alkoxy and a pharmaceutically acceptable carrier therefor.

2. A composition in accordance with claim 1 wherein $R^1$ and $R^2$ are the same or different and are hydrogen, $C_1-C_4$ alkyl, chlorine, bromine or $C_1-C_4$ alkoxy.

3. A composition in accordance with claim 2 wherein $R^1$ and $R^2$ are the same or different and are hydrogen, $C_1-C_2$ alkyl, chlorine or $C_1-C_2$ alkoxy.

4. A composition in accordance with claim 3 wherein said compound is selected from the group consisting of 1,2-dihydrazinocarbonyl-3-chlorobenzene, 1,2-dihydrazinocarbonyl-4-chlorobenzene, 2,3-dihydrazinocarbonyltoluene, 3,4-dihydrazinocarbonyltoluene, 1,2-dihydrazinocarbonyl-3-methoxybenzene and 1,2-dihydrazinocarbonyl-4-methoxybenzene.

5. A composition in accordance with claim 4 wherein said compound is 3,4-dihydrazinocarbonyltoluene.

6. A process for controlling hyperlipidemia in mammals comprising treating a mammal with a hyperlipidemia controlling effective amount of a compound having the structural formula

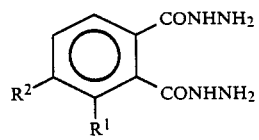

where $R^1$ and $R^2$ are the same or different and are hydrogen, $C_1-C_6$ alkyl, halogen or $C_1-C_6$ alkoxy.

7. A process in accordance with claim 6 wherein $R^1$ and $R^2$ are the same or different and are hydrogen, $C_1-C_4$ alkyl, chlorine, bromine or $C_1-C_4$ alkoxy.

8. A process in accordance with claim 7 wherein $R^1$ and $R^2$ are the same or different and are hydrogen, $C_1-C_2$ alkyl, chlorine or $C_1-C_2$ alkoxy.

9. A process in accordance with claim 8 wherein said compound is selected from the group consisting of 1,2-dihydrazinocarbonyl-3-chlorobenzene, 1,2-dihydrazinocarobnyl-4-chlorobenzene, 2,3-dihydrazinocarbonyltoluene, 3,4-dihydrazinocarbonyltoluene, 1,2-dihydrazinocarbonyl-3-methoxybenzene and 1,2-dihydrazinocarbonyl-4-methoxybenzene.

10. A process in accordance with claim 9 wherein said compound is 3,4-dihydrazinocarbonyltoluene.

11. A process in accordance with claim 6 wherein said lipidemia controlling effective amount of said compound is in the range of between about 5 and 60 milligrams per kilogram of mammalian body weight per day.

12. A process in accordance with claim 11 wherein said lipidemia controlling effective amount of said compound is in the range of between about 10 and 40 milligrams per kilogram of mammalian body weight per day.

13. A process in accordance with claim 12 wherein said lipidemia controlling effective amount of said compound is in the range of between about 15 and 30 milligrams per kilogram of mammalian body weight per day.

* * * * *